(12) United States Patent
Bauer et al.

(10) Patent No.: US 7,566,968 B2
(45) Date of Patent: Jul. 28, 2009

(54) BIOSENSOR WITH SMART CARD CONFIGURATION

(75) Inventors: Michael Bauer, Nittendorf (DE); Bernd Goller, Otterfing (DE); Robert-Christian Hagen, Sarching (DE); Gerald Ofner, Mandarin Gardens (SG); Christian Stuempfl, Schwandorf (DE); Holger Woerner, Regensburg (DE)

(73) Assignee: Siemens Aktiengesellschaft, Munich (DE)

( * ) Notice: Subject to any disclaimer, the term of this patent is extended or adjusted under 35 U.S.C. 154(b) by 315 days.

(21) Appl. No.: 11/196,497

(22) Filed: Aug. 4, 2005

(65) Prior Publication Data
US 2006/0027905 A1 Feb. 9, 2006

Related U.S. Application Data

(63) Continuation of application No. PCT/DE2004/000165, filed on Feb. 3, 2004.

(30) Foreign Application Priority Data
Feb. 5, 2003 (DE) .................. 103 04 775

(51) Int. Cl.
*H01L 23/48* (2006.01)
*H01L 23/52* (2006.01)
*H01L 29/40* (2006.01)

(52) U.S. Cl. .................. 257/734; 257/690; 257/584; 257/621; 257/784; 361/760; 361/761; 361/764; 361/767; 361/777; 361/803; 361/783

(58) Field of Classification Search .................. 257/737, 257/738, 777, 778, 584, 621, 690, 734, 784; 361/760, 761, 764, 767, 777, 778, 803
See application file for complete search history.

(56) References Cited

U.S. PATENT DOCUMENTS

| 5,120,420 | A | 6/1992 | Nankai et al. |
|---|---|---|---|
| 5,494,639 | A | 2/1996 | Grzegorzewski |
| 6,068,818 | A | 5/2000 | Ackley et al. |
| 6,396,116 | B1 * | 5/2002 | Kelly et al. .................. 257/432 |
| 6,413,474 | B1 * | 7/2002 | Igel et al. .................. 422/82.05 |
| 6,489,670 | B1 * | 12/2002 | Peterson et al. ............. 257/686 |
| 2002/0041017 | A1 | 4/2002 | Hauser et al. |
| 2002/0144554 | A1 | 10/2002 | Ueyanagi et al. |
| 2004/0115094 | A1 | 6/2004 | Gumbrecht et al. |

FOREIGN PATENT DOCUMENTS

| CA | 2 440 126 A1 | 9/2002 |
|---|---|---|
| DE | 19642488 A1 | 4/1998 |
| DE | 100 32 042 A1 | 1/2002 |
| JP | 60062978 | 4/1985 |
| WO | WO 00/23617 | 4/2000 |

* cited by examiner

*Primary Examiner*—Phuc T Dang
*Assistant Examiner*—Thanh Y Tran
(74) *Attorney, Agent, or Firm*—Harness, Dickey & Pierce, P.L.C.

(57) ABSTRACT

A biosensor that has a smart card configuration includes a semiconductor chip including a bioactive structure and contact areas disposed on a first side of the semiconductor chip, and a rewiring substrate including contact pads, external contact areas and rewiring lines that electrically connect the contact pads to the external contact areas. The rewiring substrate covers a portion of the first side of the semiconductor chip without covering the bioactive structure, such that the rewiring substrate overlaps the contact areas of the semiconductor chip and the contact pads and the contact areas are aligned with and electrically connect to each other. In addition, a measuring apparatus is configured to receive the biosensor and conduct measurements of a fluid medium that is delivered into the measuring apparatus.

10 Claims, 2 Drawing Sheets

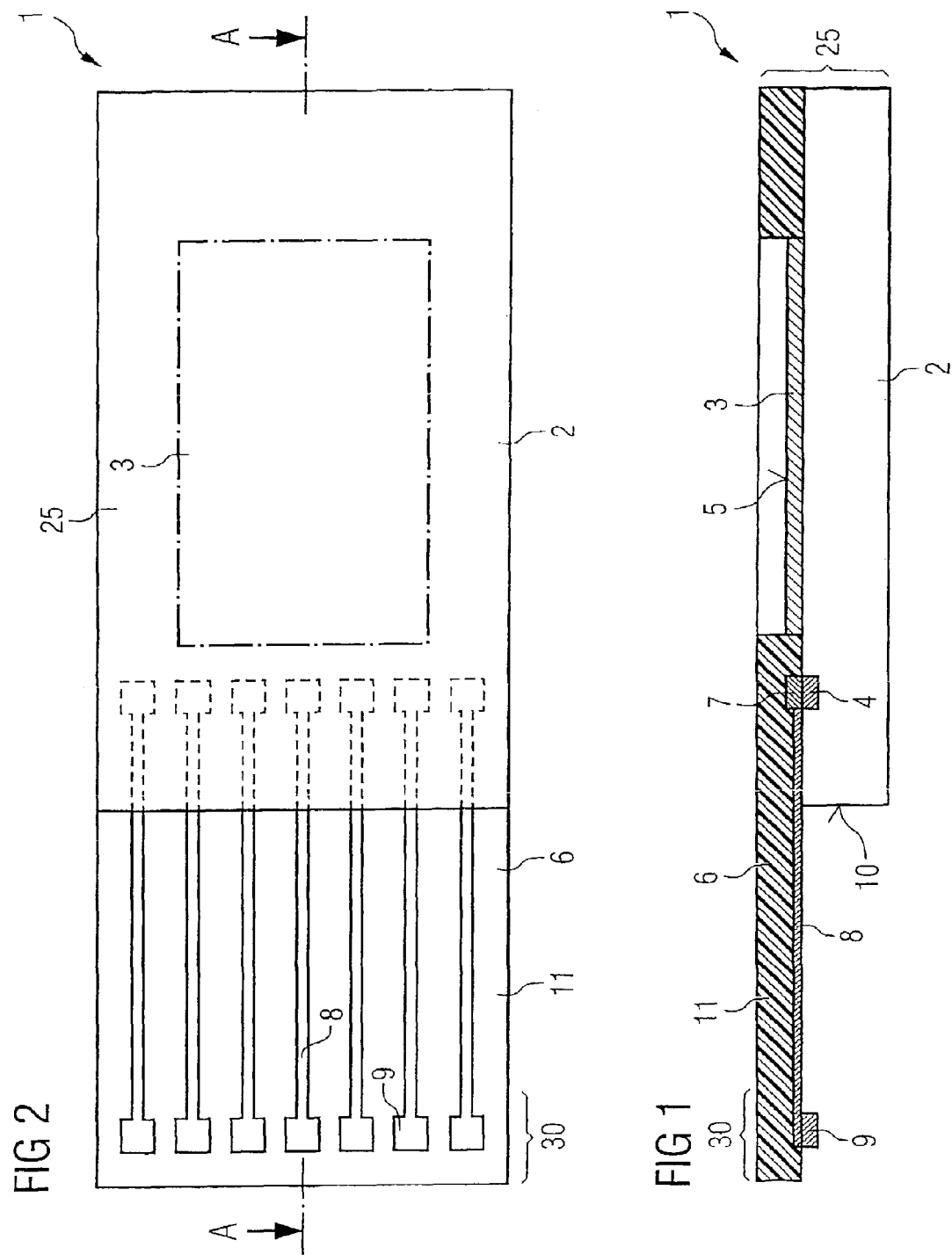

BIOSENSOR WITH SMART CARD CONFIGURATION

CROSS REFERENCE TO RELATED APPLICATIONS

This application is a continuation of PCT/DE2004/000165, filed, Feb. 3, 2004, and titled "Measuring Method for Biosensor in Smart Card Form and Method for the Production Thereof," which claims priority under 35 U.S.C. § 119 to German Application No. 103 04 775.1, filed on Feb. 5, 2003, and titled "Measuring Method for Biosensor in Smart Card Form and Method for the Production Thereof," the entire contents of which are hereby incorporated by reference.

FIELD OF THE INVENTION

The invention relates to a measuring apparatus and a measuring method for biosensors in smart card form and method for the production thereof.

BACKGROUND

Biosensors based on semiconductor chips have bioactive structures which react to different ambient influences. For this purpose, the semiconductor chips have surface structures which are sensitive to gases and liquids or aerosols, and which are particularly sensitive to biological substances such as lymph fluid, blood, urine and other bodily fluids. Biosensors of a conventional type are cost-intensive.

SUMMARY OF THE INVENTION

It is an object of the invention to provide a cost-effective measuring apparatus as a disposable product for serial examinations of bodily fluids.

The above and further objects are achieved in accordance with the invention with a biosensor having the following features. A semiconductor chip is provided comprising a bioactive structure on its top side, and contact areas having access to the bioactive structure. Arranged on the top side of the semiconductor chip is a rewiring substrate including contact pads that are connected to external contact areas via rewiring lines of the rewiring substrate. The rewiring substrate covers the top side of the semiconductor chip while leaving the bioactive structure free. The contact areas of the semiconductor chip are covered by the contact pads in such a way that contact pads and contact areas lie one on top of the other and are electrically connected to one another.

In accordance with another embodiment of the invention, a method for the production of a biosensor in a smart card configuration includes the following method steps. First, a semiconductor chip including a bioactive structure is produced and provided with contact areas on its top side which have access to the bioactive structure. A bioactive structure of this type can include resistance measuring electrodes, capacitive measuring elements or inductive measuring elements or other structures that react with biological media. After the production of a suitable semiconductor chip, a rewiring substrate including contact pads is produced. The contact pads correspond to the contact areas on the top side of the semiconductor chip with respect to their arrangement and size. The contact areas can be arranged in a row in an edge region of the semiconductor chip, so that the contact pads also have to be provided in only one row.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components. While these descriptions go into specific details of the invention, it should be understood that variations may and do exist and would be apparent to those skilled in the art based on the descriptions herein.

BRIEF DESCRIPTION OF THE DRAWINGS

FIG. 1 depicts a cross-sectional schematic view through a smart card of a biosensor along the sectional line A-A of FIG. 2.

FIG. 2 depicts a bottom view of the smart card in accordance with FIG. 1.

DETAILED DESCRIPTION

Figure 3:
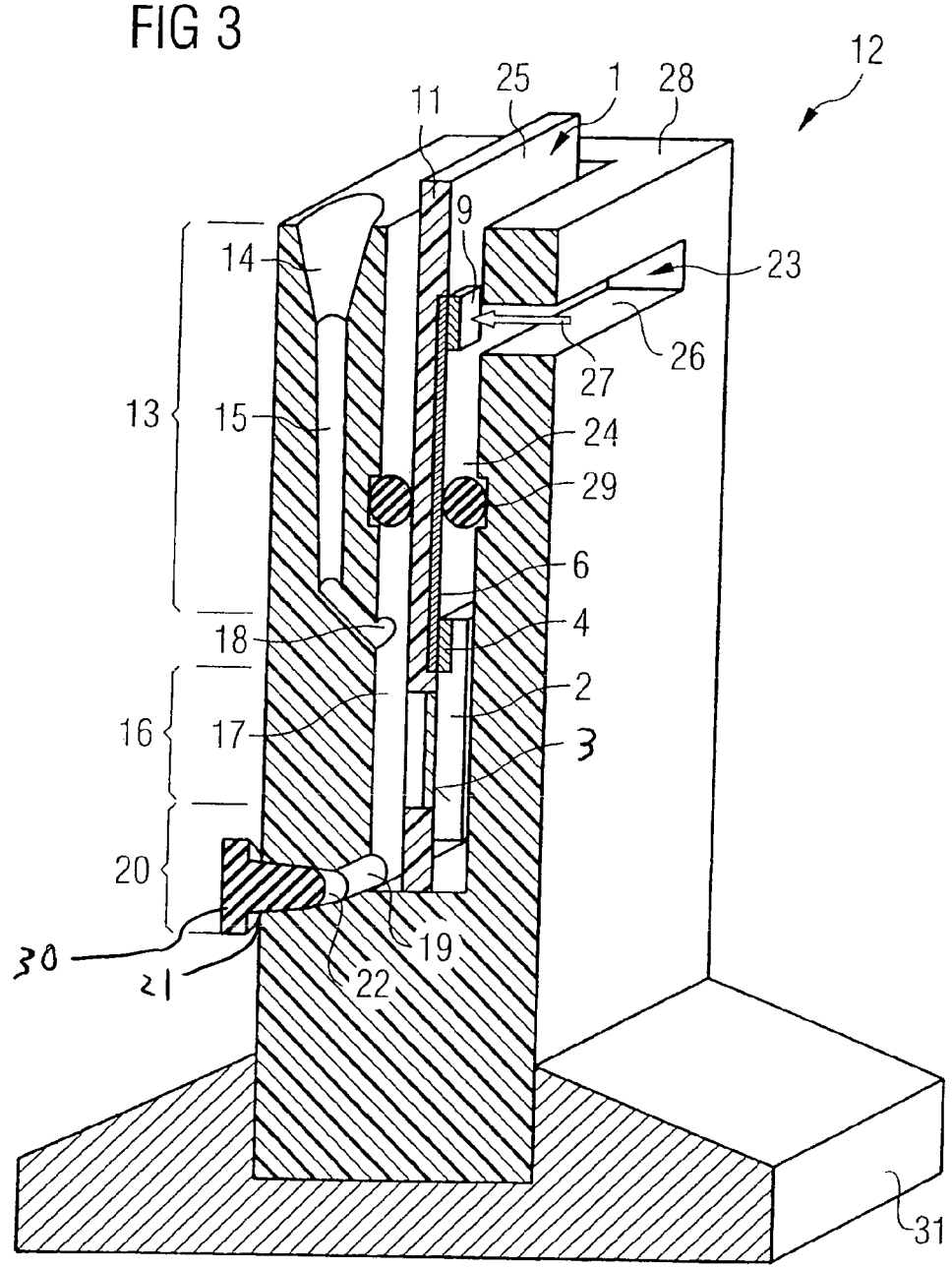
FIG. 3 depicts a schematic cross-sectional view in perspective of a measuring apparatus with inserted smart card in accordance with FIG. 1.

A biosensor in accordance with the invention includes a semiconductor chip with a bioactive structure on its top side, and contact areas having access to the bioactive structure. The bioactive structure is sensitive to gases and liquids or aerosols, such as biological substances like lymph fluid, blood, urine and other bodily fluids. Any suitable bioactive structure known in the art can be provided in the biosensor of the present invention to facilitate detection and/or concentration measurements of any one or more biological substances within a fluid to be analyzed by the biosensor.

Arranged on the top side of the semiconductor chip is a rewiring substrate including contact pads that are connected to external contact areas via rewiring lines of the rewiring substrate. The rewiring substrate covers the top side of the semiconductor chip while leaving the bioactive structure free. The contact areas of the semiconductor chip are covered by the contact pads in such a way that contact pads and contact areas lie one on top of the other and are electrically connected to one another.

Components of the biosensor can largely be melted down after use in order to reuse the raw materials employed. As a result, it is possible to avoid any cost-intensive cleaning and sterilization, particularly in the case of critical blood and lymph fluid examinations.

One advantage of the biosensor according to the invention is that the rewiring substrate used can be an inexpensive film patterned and coated on one side and made of insulation material or made of a plastic plate which corresponds in its size to a smart card and can thus be produced inexpensively.

The rewiring substrate, which is made of a film or smart card material, can surround the bioactive region on the semiconductor chip and project beyond an edge of the semiconductor chip. External contact areas are arranged at a distance from the semiconductor chip on the projecting region of the rewiring substrate. Despite the external contact areas being spaced apart from the semiconductor chip and the bioactive region in this manner, an access to the bioactive structure of the semiconductor chip is possible via the external contact areas and the rewiring lines that are arranged on the same side to the contact pads and thus to the contact areas of the semiconductor chip, which is an extremely simple and cost-effective.

Further, the rewiring substrate that covers the entire top side of the semiconductor chip apart from the region of the bioactive structure forms a smart card which constitutes a composite of insulation material and semiconductor material in a reliable and stable manner.

Such cost-effectively patterned rewiring substrates and semiconductor chips result in a disposable product that is suitable for serial examinations and completely precludes the transfer of germs during the examination of bodily fluids.

In order to provide a measuring apparatus for a biosensor of this type, where the measuring apparatus is essentially composed of material that can be melted down and reused but is simplified in terms of its construction in such a way that it can be produced cost-effectively in large quantities, the dimensions of the measuring apparatus are closely adapted to the design of the biosensor in smart card configuration. A measuring apparatus of this type has an inlet region including an entry opening for the medium to be measured. An entry channel extends from the entry opening as far as a sensor region. A measurement cavity is provided in the sensor region of the measuring apparatus, and the entry channel extends to the measurement cavity such that medium to be measured can be fed to the measurement cavity.

The measurement cavity includes an outflow opening such that the medium to be measured can be discharged to the greatest possible extent after measurement has been achieved. In an exit region, an exit channel extends from the outflow opening of the measurement cavity to an exit opening. The exit opening can be closed off using a simple device (e.g., a plug) during the actual measurement. In addition to these three regions, which are wetted by the medium to be measured, a further region is provided outside the measurement cavity as a sensing region.

The sensing region includes an insertion channel for inserting a smart card including a biosensor and includes a sensing cavity with sensing contact elements. The insertion channel is spatially connected to the measurement cavity. After a smart card has been inserted into the insertion channel, the sensing contact elements can be brought into contact with the external contact areas of the smart card.

A measuring apparatus of this type has the advantage that it can be constructed extremely flat. Apart from the sensing elements in the sensing cavity, it is composed only of a plastics composition with hollow spaces in the form of channels and cavities. Consequently, a flat measuring apparatus of this type can be produced in large quantities by known injection molding methods or compression molding methods. In this case, the complete measuring apparatus can be produced, with the sensing region being incorporated and embedded, by means of a single injection molding step.

A measuring apparatus of this type does not have to be larger in construction than a conventional smart card receptacle pocket, which is made only a few millimeters thicker than the smart card itself and a few millimeters larger in extent than the biosensor in the form of the smart card. For this purpose, the inlet region, the sensor region, the sensing region and the exit region are arranged in a measuring apparatus housing having the dimensions specified above. In this case, the sensor region forms a spatial center of the measuring apparatus, since both the insertion channel and the entry channel are led toward this center and the exit channel leads away from this center.

Further, the regions that are wetted by the medium to be measured, such as the inlet region, the sensor region and the exit region, can be arranged in such a way that the force of gravity transports the medium to be measured through the measuring apparatus. This is advantageous particularly for the examination of bodily fluids, since there is no need to provide any additional drive units for the throughflow of the fluids to be measured, so that the measuring apparatus can be constructed from fully passive components that can be produced cost-effectively.

In order to prevent the medium to be measured from penetrating into the sensing region, a seal can be arranged between the measurement cavity and the sensing cavity. The seal can be concomitantly shaped as lips during the injection molding process or it can be provided separately in corresponding cutouts in the boundary region of measurement cavity and sensing cavity. A seal of this type is particularly advantageous if aerosols and gases are to be examined, since the measurement cavity is then separated from the sensing cavity and the insertion channel by the seal. The plastic used for the measuring apparatus housing is preferably a thermoplastic which can be melted down directly and then reutilized after measurement has been achieved.

When the thermoplastics are melted down, a sufficiently high temperature is employed to destroy all germs. Before the melting down process, only the sensing contact elements are removed from the sensing cavity, which may be effected by simply etching or by locally heating and pulling off the sensing contact elements. Sensing elements of this type can be constructed and implemented by simple sliding-action contacts or spring contacts made of spring bronze which, upon insertion of a biosensor in smart card configuration, produce a sliding-action contact or a spring contact with the external contact areas of the rewiring plate. A somewhat more complex solution is afforded by a mechanical feedback between sensing contact elements and the smart card's insertion operation. By providing simple chip elements in the insertion channel, the sensing elements are brought into contact with the external contact areas only if the smart card has reached its final position in the measurement cavity. By providing an optoelectronic feedback, the signal required for contact-making can be achieved with no actual contacts.

In a preferred embodiment, a reusable sensing unit is positioned in the sensing cavity of the sensing region. This provides the advantage that a relatively small sensing and measuring unit has to be cleaned and sterilized after the measurement operation, while the plastic housing itself is supplied for further utilization by melting down the plastics composition.

A method for the production of a biosensor in a smart card configuration includes the following method steps. First, a semiconductor chip including a bioactive structure is produced and provided with contact areas on its top side which have access to the bioactive structure. A bioactive structure of this type can include resistance measuring electrodes, capacitive measuring elements or inductive measuring elements or other structures that react with biological media. After the production of a suitable semiconductor chip, a rewiring substrate including contact pads is produced. The contact pads correspond to the contact areas on the top side of the semiconductor chip with respect to their arrangement and size. The contact areas can be arranged in a row in an edge region of the semiconductor chip, so that the contact pads also have to be provided in only one row.

The contact pads are connected to external contact areas via rewiring lines. A photolithography step or a screen printing step can be used for such patterning of the rewiring substrate. In this case, an insulation film coated on one side is patterned by etching and the use of a mask. The screen printing method, in particular, is a mass production method that can be carried out inexpensively.

After the production of the rewiring substrate, the rewiring substrate is connected to the semiconductor chip with the bioactive structure being left free. This connection can be carried out by thermocompression methods, particularly if the rewiring substrate is likewise composed of a thermoplastic. On the other hand, lamination with an adhesive layer arranged between the rewiring substrate and the semiconductor chip surface is possible.

In order to enable access to the external contact areas in an extremely simple manner, the latter are provided in a region of the rewiring substrate which projects beyond the semiconductor chip. The length of this projecting rewiring region is adapted to the length of the insertion channel and the extent of the sensor region of the measuring apparatus described above. This length is dimensioned such that the external contact areas are not wetted by the medium to be measured when the biosensor has been inserted into the measuring apparatus described above.

A measuring method for measuring biological media samples with the measuring apparatus described above includes the following method steps. First, a smart card including a biosensor is inserted into the insertion channel of the measuring apparatus while contact-connecting the external contact areas of the smart card to the sensing contact elements of the measuring apparatus. Afterward, the media sample is introduced into the entry opening and is distributed in the measuring apparatus via the entry channel and the measurement opening in the measurement cavity. In the measurement cavity, the medium to be measured washes round or wets the bioactive structure of the semiconductor chip sensor and can be discharged from the exit opening via the outflow opening and the exit channel after the measurement.

During the measurement, either the semiconductor chip itself can store the measurement data, so that they can be analyzed in an evaluation apparatus once the smart card has been removed, or the measured values can be transmitted to a corresponding evaluation unit directly via the sensing contact elements. After the measurement, the hollow spaces and channels which came into contact with the media sample can be rinsed and/or disinfected in a simple manner. However, it is preferred, in the case of critical bodily fluids, for the entire measuring apparatus to be melted down after the separation of the sensing contact elements, in order to avoid any transfer of germs.

Thus, the biosensor of the present invention includes a biochip, with a patterned film or rewiring substrate including a corresponding rewiring structure that is applied to the bonding pads or contact areas of the biochip. As note above, application of this patterned film can be applied by a thermocompression method or by lamination. Thus, the biosensor region in the form of a bioactive structure remains free of the rewiring film. Further, the device according to the invention includes a measuring apparatus with which the external contact areas or terminal pads of the rewiring film are electrically contact-connected. Besides sliding-action contacts, this contact-connection of the terminal pads can also be achieved by using needle cards and pogopins or the like.

The coordination of the order of magnitude of a smart card with biosensor and of a corresponding measuring apparatus enables a disposable article that can be produced more cost-effectively than is possible in the case of biosensors with corresponding measuring apparatuses conventionally known in the art.

An exemplary embodiment of a biosensor in a smart card configuration that can be used with a measuring apparatus is described below and depicted in FIGS. 1-3. In particular, FIG. 1 shows a schematic cross-section through a smart card 25 of a biosensor 1. Smart card 25 includes a semiconductor chip 2 with a bioactive structure 3 on its top side 5. A bioactive structure 3 of this type has an area of between 1×1 mm² and 5×5 mm². Although even smaller biosensor structures are possible, the accuracy of the measurable signals increases as the sensor area increases.

In the vicinity of an edge 10 of the semiconductor chip 2, contact areas are arranged in a row on the top side 5, where the contact areas enable access to the bioactive structure 3. A rewiring substrate 6 is arranged on the top side 5 of the semiconductor chip 2. The rewiring substrate includes, on one side, a rewiring structure including contact pads 7, rewiring lines 8 and external contact areas 9. The rewiring substrate is oriented with its external contact pads 7 aligned with the contact areas 4 of the semiconductor chip 2. As can be seen in FIG. 1, the rewiring substrate 6 surrounds but does not cover bioactive structure 3.

The contact areas 4 and the contact pads 7 are electrically connected to one another. The rewiring substrate 6 extends with a projecting region 11 beyond the edge 10 of the semiconductor chip 2. This projecting region 11 has external contacts 9 in an edge region 30 of the rewiring substrate, so that there is a possibility of access to the external contacts 9.

FIG. 2 shows a bottom view of the smart card 25 in accordance with FIG. 1. This bottom view shows the rear side of the semiconductor chip 2, which covers both the contact pads 7 and the contact areas 4, and also the bioactive region 3. Therefore, the position of the contact pads 7 and of the contact areas 4 is illustrated merely by dashed lines and the bioactive region 3 is identified by a dash-dotted line. The remaining region of the semiconductor chip 2 is completely covered by the rewiring substrate 6, which, in this embodiment of the invention, is formed from a rewiring film with a single-sided rewiring structure. Only the underside of the rewiring substrate 6 in the projecting region 11 can be seen completely in FIG. 2, so that the external contacts 9 and the rewiring lines 8 can be seen. In this embodiment of the invention, the rewiring lines 8 run parallel to one another and connect the semiconductor chip to the external contacts 9 of the rewiring substrate 6.

FIG. 3 shows a schematic cross-sectional view in perspective of a measuring apparatus 12 with inserted smart card 25 of FIG. 1. The measuring apparatus 12 includes an inlet region 13, a sensor region 16, an outlet region 20 and a sensing region 23. The inlet region 13 has an entry opening 14 and an entry channel 15 leading to the sensor region 16. The sensor region itself includes a measurement cavity 17, into which leads a measurement opening 18 at the end of the entry channel 15. Furthermore, the measurement cavity 17 includes an outflow opening 19, which merges with the exit region 20 having an exit channel 22 and an exit opening 21. A removable plug 30 is inserted within exit channel 22 to prevent fluid from flowing from the exit channel during a measurement procedure. When the plug 30 is removed, fluid is permitted to flow through exit channel 22 and out of opening 21. Thus, when smart card 25 is inserted within measuring apparatus 12, as shown in FIG. 3, bioactive structure 3 of the smart card is in fluid communication with measurement cavity 17.

While the entry region 13, the sensor region 16 and the exit region 20 are wetted by the medium to be measured, the sensing region 23 remains free of the medium to be measured. The sensing region 23 merges with an insertion channel 24 for a smart card 25 and includes a sensing cavity 26, in which sensing contact elements 27 are arranged. The sensing contact elements 27 can include needle cards or pogopins or, alternatively, spring contacts or sliding-action contacts. When a smart card 25 is inserted into the insertion channel 24, the contact elements 27 of the measuring apparatus 12 come into contact with the external contact areas 9 of the smart card 25.

The cavities and channels are formed in a measurement housing 28 made of a suitable plastics composition. The measurement housing 28 is produced from a thermoplastic by, e.g., a compression molding method. The measurement housing 28 is melted down after the measurement operation and the withdrawal of the smart card 25 and after the removal of the sensing contact elements 27 from the sensing region 23. A plastic housing 28 of this type can be produced inexpensively in mass production, so that cleaning the channels and cavities proves to be simple and relatively inexpensive. Melting down the thermoplastic plastics composition of the measurement housing 28 destroys all germs that may still adhere to the plastic material with the medium to be measured after the medium has been discharged from the exit opening 21.

A measuring apparatus of this type is a few millimeters wide and a few millimeters larger in its areal extent than the smart card 25. In order to enable reliable handling of the measuring apparatus 12, however, a plug-in base 31 is provided, which receives one or more of the measuring apparatuses 12 in one or more grooves provided within the base. The plug-in base 31 ensures that the medium to be measured, particularly if liquids are involved, is transported through the measuring apparatus housing 28 by the force of gravity.

In the embodiment of FIG. 3, the measurement cavity 17 is separated from the sensing region 23 by a seal 29 in the region of the insertion channel 24. A seal 29 of this type is provided particularly when measuring liquids having a high vapor pressure. For liquids having a low vapor pressure, it is possible to eliminate the seal 29, which additionally reduces the costs for a measuring apparatus of this type.

Media sample measurements (e.g., presence and/or concentrations of biological substances within the media sample measured within the measuring apparatus) can be stored (e.g., via a processor with memory) on one or both the biosensor and the measuring apparatus. Further, the media sample measurements can also be displayed via a suitable display provided on one or both the biosensor and the measuring apparatus.

While the invention has been described in detail and with reference to specific embodiments thereof, it will be apparent to one skilled in the art that various changes and modifications can be made therein without departing from the spirit and scope thereof. Accordingly, it is intended that the present invention covers the modifications and variations of this invention provided they come within the scope of the appended claims and their equivalents.

What is claimed is:

1. A biosensor comprising:
a semiconductor chip including a bioactive structure and contact areas disposed on a first side of the semiconductor chip; and
a rewiring substrate including contact pads, external contact areas and rewiring lines that electrically connect the contact pads to the external contact areas;
wherein the rewiring substrate is directly positioned on and covers a portion of the first side of the semiconductor chip without covering the bioactive structure such that the rewiring substrate overlaps the contact areas of the semiconductor chip, and the contact pads of the rewriting substrate and the contact areas of the semiconductor chip are positioned directly on, aligned with and electrically connected to each other.

2. The biosensor of claim 1, wherein the rewiring substrate surrounds the bioactive structure and includes a projecting region that projects beyond an edge of the semiconductor chip, and the external contact areas are arranged on the projecting region of the rewiring substrate.

3. The biosensor of claim 1, wherein the contact pads, external contact areas and rewiring lines are all arranged on a single side of the rewiring substrate.

4. A measuring apparatus for a biosensor having a semiconductor chip including a bioactive structure and contact areas disposed on a first side of the semiconductor chip, and a rewiring substrate including contact pads, external contact areas and rewiring lines that electrically connect the contact pads to the external contact areas, the measuring apparatus comprising:
an inlet region including an entry opening to receive a medium to be measured and an entry channel in fluid communication with the inlet region;
a fluid flow and measuring region including a measurement cavity, a measurement opening in fluid communication with the entry channel to facilitate flow of the medium into the measurement cavity, and an outflow opening in fluid communication with the measurement cavity;
an exit region including an exit opening and an exit channel extending between the outflow opening of the fluid flow and measuring region and the exit opening;
a sensing region comprising an insertion channel to receive the biosensor, and a sensing cavity including sensing contact elements;
wherein the insertion channel of the sensing region is spatially adjacent the measurement cavity of the fluid flow and measuring region such that, upon insertion of the biosensor within the measuring apparatus, the biosensor divides and separates the insertion channel from the measurement cavity;
upon insertion of the biosensor within the insertion channel of the sensing region, the sensing contact elements within the sensing cavity of the sensing region are brought into contact with the external contact areas of the biosensor; and
the rewiring substrate covers a portion of the first side of the semiconductor chip without covering the bioactive structure such that the rewiring substrate overlaps the contact areas of the semiconductor chip, and
the contact pads of the rewriting substrate and the contact areas of the semiconductor chip are aligned with and electrically connected to each other.

5. The measuring apparatus of claim 4, wherein the inlet region, the fluid flow and measuring region, the exit region, and the sensing region are all arranged in a housing of the measuring apparatus.

6. The measuring apparatus of claim 4, wherein the fluid flow and measuring region is arranged at a spatial center of the measuring apparatus.

7. The measuring apparatus of claim 4, wherein the inlet region, the fluid flow and measuring region and the exit region are all arranged within the measuring apparatus such that the force of gravity transports the medium to be measured through the measuring apparatus.

8. The measuring apparatus of claim 4, further comprising: a seal arranged between the measurement cavity and the sensing cavity.

9. A method for measuring biological media samples utilizing the measuring apparatus of claim 4, the method comprising the following steps: inserting the biosensor into the insertion channel of the measuring apparatus so as to electrically contact the external contact areas of the biosensor with the sensing contact elements of the measuring apparatus; introducing the media sample into the entry opening of the inlet region of the measuring apparatus; conducting measurements of the media sample with the biosensor; and conducting at least one of storing media sample measurements on the smart card or the measuring apparatus and displaying media sample measurements.

10. The method of claim 9, wherein the media sample measurements are stored, and the method further comprises: discharging the media sample via the exit channel and the exit opening of the exit region; and rinsing and/or disinfecting the inlet region, the fluid flow and measuring region and the exit region of the measuring apparatus.

* * * * *